United States Patent
Rathnakar Reddy et al.

(10) Patent No.: US 12,187,740 B2
(45) Date of Patent: Jan. 7, 2025

(54) POLYMORPHIC FORMS OF BICTEGRAVIR POTASSIUM

(71) Applicant: HONOUR LAB LIMITED, Hyderabad (IN)

(72) Inventors: Kura Rathnakar Reddy, Hyderabad (IN); Kesireddy Subhash Chander Reddy, Hyderabad (IN); Guda Yadav Reddy, Hyderabad (IN)

(73) Assignee: HONOUR LAB LIMITED, Hyderabad (IN)

( * ) Notice: Subject to any disclaimer, the term of this patent is extended or adjusted under 35 U.S.C. 154(b) by 0 days.

(21) Appl. No.: 18/555,782

(22) PCT Filed: Apr. 18, 2022

(86) PCT No.: PCT/IB2022/053604
§ 371 (c)(1),
(2) Date: Oct. 17, 2023

(87) PCT Pub. No.: WO2022/224120
PCT Pub. Date: Oct. 27, 2022

(65) Prior Publication Data
US 2024/0208995 A1    Jun. 27, 2024

(30) Foreign Application Priority Data
Apr. 19, 2021   (IN) .............................. 202141017972

(51) Int. Cl.
*C07D 498/14*    (2006.01)
*C07D 498/18*    (2006.01)
(52) U.S. Cl.
CPC ................................ *C07D 498/18* (2013.01)

(58) Field of Classification Search
CPC .......................... C07D 498/14; C07B 2200/13
USPC .......................................................... 540/546
See application file for complete search history.

(56) References Cited

U.S. PATENT DOCUMENTS

| | | |
|---|---|---|
| 9,216,996 B2 | 12/2015 | Jin et al. |
| 9,682,084 B2 | 6/2017 | Carra et al. |
| 11,623,933 B2 * | 4/2023 | Rathnakar Reddy ....................... C07D 498/18 540/546 |
| 2015/0366872 A1 | 12/2015 | Carra et al. |

FOREIGN PATENT DOCUMENTS

| | | | |
|---|---|---|---|
| CN | 111978333 A | 11/2020 | |
| IN | 201941032384 A | 2/2021 | |
| WO | 2015196116 A1 | 12/2015 | |
| WO | WO2015196116 | * 12/2015 | ........... C07D 498/14 |
| WO | WO2015196137 | * 12/2015 | ........... C07D 498/14 |
| WO | 2019154634 A1 | 8/2019 | |
| WO | 2020003151 A1 | 1/2020 | |
| WO | 2021233434 A1 | 11/2021 | |

OTHER PUBLICATIONS

English Abstract for CN 111978333 A (2020).
International Search Report for PCT/IB2022/053604 dated Jun. 29, 2022.

* cited by examiner

*Primary Examiner* — Jeffrey H Murray
(74) *Attorney, Agent, or Firm* — Caesar Rivise, PC

(57) ABSTRACT

The present invention relates to polymorphic forms of Bictegravir potassium of Formula II, process for their preparation and pharmaceutical composition comprising it.

9 Claims, 2 Drawing Sheets

POLYMORPHIC FORMS OF BICTEGRAVIR POTASSIUM

CROSS-REFERENCE TO RELATED APPLICATIONS

This application is a U.S. National Phase Application of PCT/IB2022/053604, filed Apr. 18, 2022, which claims priority from IN 202141017972, filed Apr. 19, 2021, the contents of which applications are incorporated herein by reference in their entireties for all purposes.

FIELD OF THE INVENTION

The present invention relates to polymorphic forms of Bictegravir potassium salt and process for the preparation thereof.

BACKGROUND OF THE INVENTION

Sodium (2R,5S,13aR)-7,9-dioxo-10-((2,4,6-trifluorobenzyl)carbamoyl)-2,3,4,5,7,9,13,13a-octahydro-2,5-Methanopyrido[1',2':4,5]pyrazino[2,1-b][1,3]oxazepin-8-olate is known to be Bictegravir sodium of Formula I, which has been approved as the combination drug in US as Bictegravir; Emtricitabine; Tenofovir alafenamide under the trade name of BIKTARVY® for treating HIV.

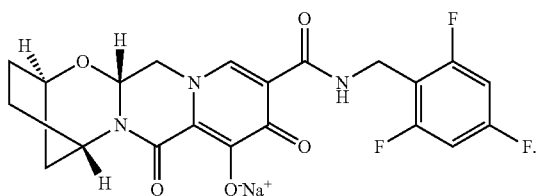

Formula I (2R,5S,13aR)-7,9-dioxo-10-((2,4,6-trifluorobenzyl) carbamoyl)-2,3,4,5,7,9,13,13a-octahydro-2,5-methanopyrido[1',2':4,5]pyrazino[2,1-b][1,3] oxazepin-8-olate as well as its pharmaceutically acceptable salts are first known in U.S. Pat. No. 9,216,996 B2. (US'996).

US '996 has disclosed the following process for the preparation of (2R,5S,13aR)-7,9-dioxo-10-((2,4,6-trifluorobenzyl) carbamoyl)-2,3,4,5,7,9,13,13a-octahydro-2,5-Methanopyrido[1',2':4,5]pyrazino[2,1-b][1,3] oxazepin-8-olate:

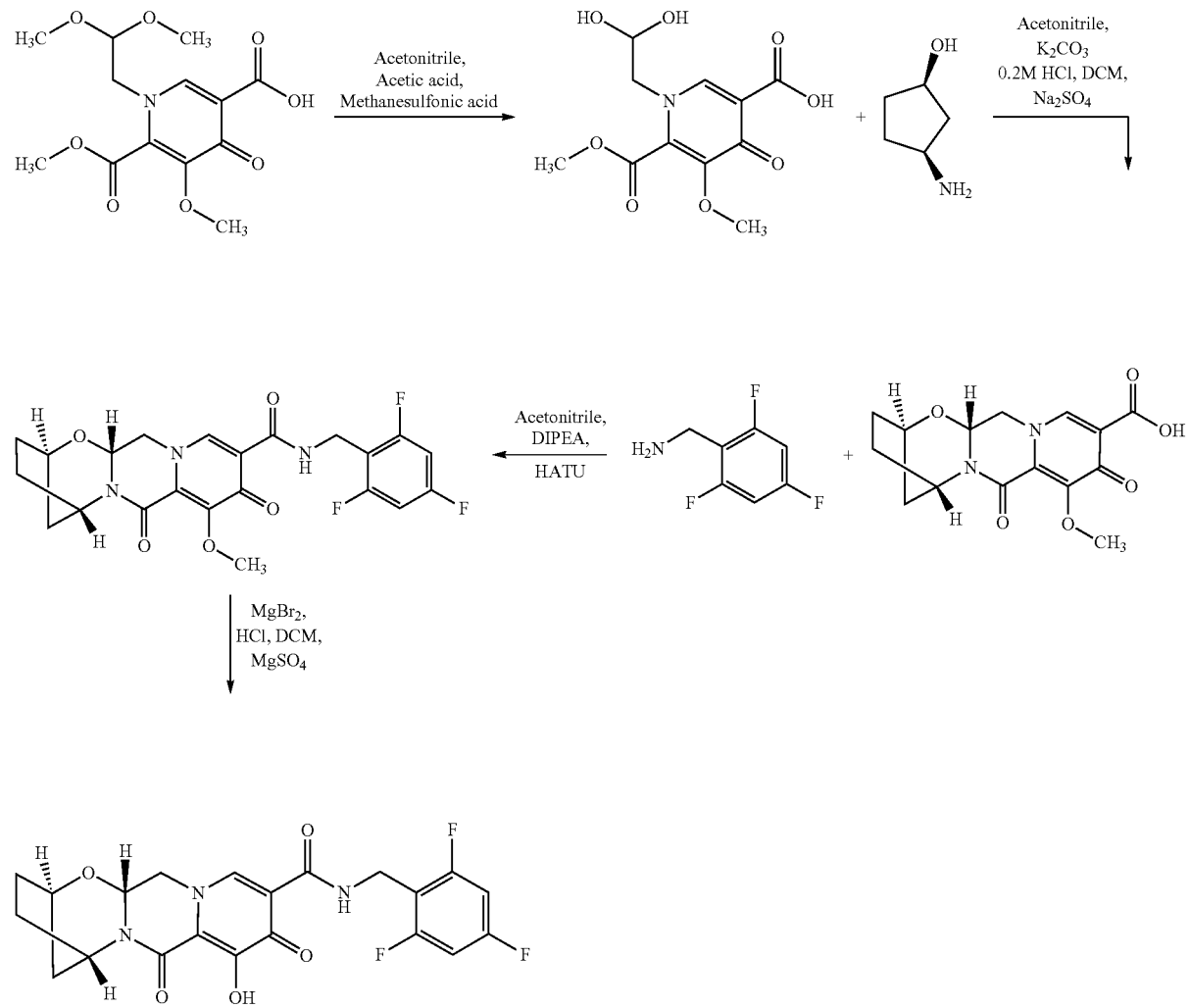

US'996 has disclosed pharmaceutically acceptable salts of (2R,5S,13aR)-7,9-dioxo-10-((2,4,6-trifluorobenzyl) carbamoyl)-2,3,4,5,7,9,13,13a-octahydro-2,5-methanopyrido [1',2':4,5]pyrazino[2,1-b][1,3] oxazepin-8-olate, however there is no exemplification of potassium salt of (2R,5S, 13aR)-7,9-dioxo-10-((2,4,6-trifluorobenzyl) carbamoyl)-2, 3,4,5, 7,9,13,13a-octahydro-2,5-Methanopyrido[1',2':4,5] pyrazino[2,1-b][1,3] oxazepin-8-olate.

Polymorphism is defined as "the ability of a substance to exist as two or more crystalline phases that have different arrangement and/or conformations of the molecules in the crystal Lattice. Thus, in the strict sense, polymorphs are different crystalline structures of the same pure substance in which the molecules have different arrangements and/or different configurations of the molecules". Different polymorphs may differ in their physical properties such as melting point, solubility, X-ray diffraction patterns, etc. Although those differences disappear once the compound is dissolved, they can appreciably influence pharmaceutically relevant properties of the solid form, such as handling properties, dissolution rate and stability. Such properties can significantly influence the processing, shelf life, and commercial acceptance of a polymorph. It is therefore important to investigate all solid forms of a drug, including all polymorphic forms, and to determine the stability, dissolution and flow properties of each polymorphic form. Polymorphic forms of a compound can be distinguished in the laboratory by analytical methods such as X-ray diffraction (XRD), Differential Scanning calorimetry (DSC) and Infrared spectrometry (IR).

U.S. Pat. No. 9,682,084 B2 discloses the polymorphic forms of the (2R,5S,13aR)-7,9-dioxo-10-((2,4,6-trifluorobenzyl) carbamoyl)-2,3,4,5,7,9,13,13a-octahydro-2,5-Methanopyrido [1',2':4,5] pyrazino [2,1-b] [1,3] oxazepin-8-olate, potassium salt of Formula II designated as Form-I, Form-II, Form-III and hydrate having five to six water molecules, however this patent is silent about Powder X-Ray Diffraction pattern and characteristic peaks.

Formula II

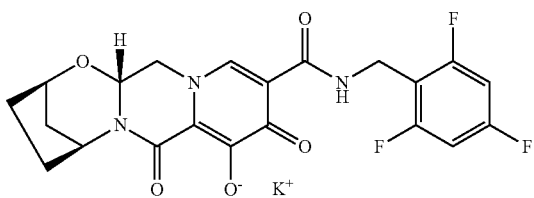

IN 201941032384 discloses bictegravir potassium Form M1 characterized by peaks at 2-theta 6.38, 9.17, 15.63 and 19.24±0.2° and is prepared by dissolving bictegravir base in alcohol solvent and treating with potassium source and thereafter isolating Bictegravir potassium Form M1.

Bictegravir potassium salt can exist in different polymorphic forms which may have properties such as bioavailability and stability at certain conditions that may be suitable for medical or pharmaceutical uses, may differ from each other in terms of stability, physical properties, spectral data as well as process for the preparation thereof.

In view of this, the present inventors have now found a process suitable industrially for preparing polymorphic forms of Bictegravir potassium salt which is stable, reproducible, free of other polymorphic forms and suitable for pharmaceutical composition.

OBJECTIVES OF THE INVENTION

The objective of the present invention is to provide crystalline forms of Bictegravir potassium.

Another objective of the present invention is to provide a process for the preparation of crystalline forms of Bictegravir potassium which are industrially applicable and economically viable.

SUMMARY OF THE INVENTION

The present invention relates to Bictegravir potassium crystalline Form HN1 having the X-ray powder diffraction pattern shown in FIG. 1 and having characteristic 2θ peaks at 6.8 and 18.1±0.2°.

The present invention relates to a process for the preparation of Bictegravir potassium crystalline Form HN1, which comprises:
  a. dissolving Bictegravir in a solvent;
  b. adding potassium source; and
  c. isolating Bictegravir potassium crystalline Form HN1 characterized by Powder X-Ray diffraction pattern, shown in FIG. 1 and having characteristic 2θ peaks at 6.8 and 18.1±0.2°;
  wherein the solvent is selected from group comprising halogenated hydrocarbon solvent, water, alcohol and mixtures thereof.

In another embodiment, present invention relates to Bictegravir potassium crystalline Form HN2 having the X-ray powder diffraction pattern shown in FIG. 2 and having characteristic 2θ peaks at 5.2 and 5.8±0.2°.

The present invention relates to a process for the preparation of Bictegravir potassium crystalline Form HN2, which comprises:
  a. dissolving of Bictegravir in halogenated hydrocarbon solvent, water and mixtures thereof;
  b. adding potassium source; and
  c. isolating Bictegravir potassium crystalline Form HN2 characterized by Powder X-Ray diffraction pattern shown in FIG. 2 and having characteristic 2θ peaks at 5.2 and 5.8±0.2°.

Powder X-Ray Diffraction Method:

X-ray powder diffraction spectrum was measured on a BRUKER axs D8 advance X-ray powder diffractometer having a copper-Ka radiation. Approximately 1 gm of sample was gently flattered on a sample holder and scanned from 2 to 50 degrees two-theta, at 0.02 degrees two theta per step and a step time of 10.8 seconds. The sample was simply placed on the sample holder. The sample was rotated at 30 rpm at a voltage 40 KV and current 35 A.

DETAILED DESCRIPTION OF THE INVENTION

The present invention relates to different crystalline forms of Bictegravir potassium designated as Form HN1 and Form HN2.

Figure 1:
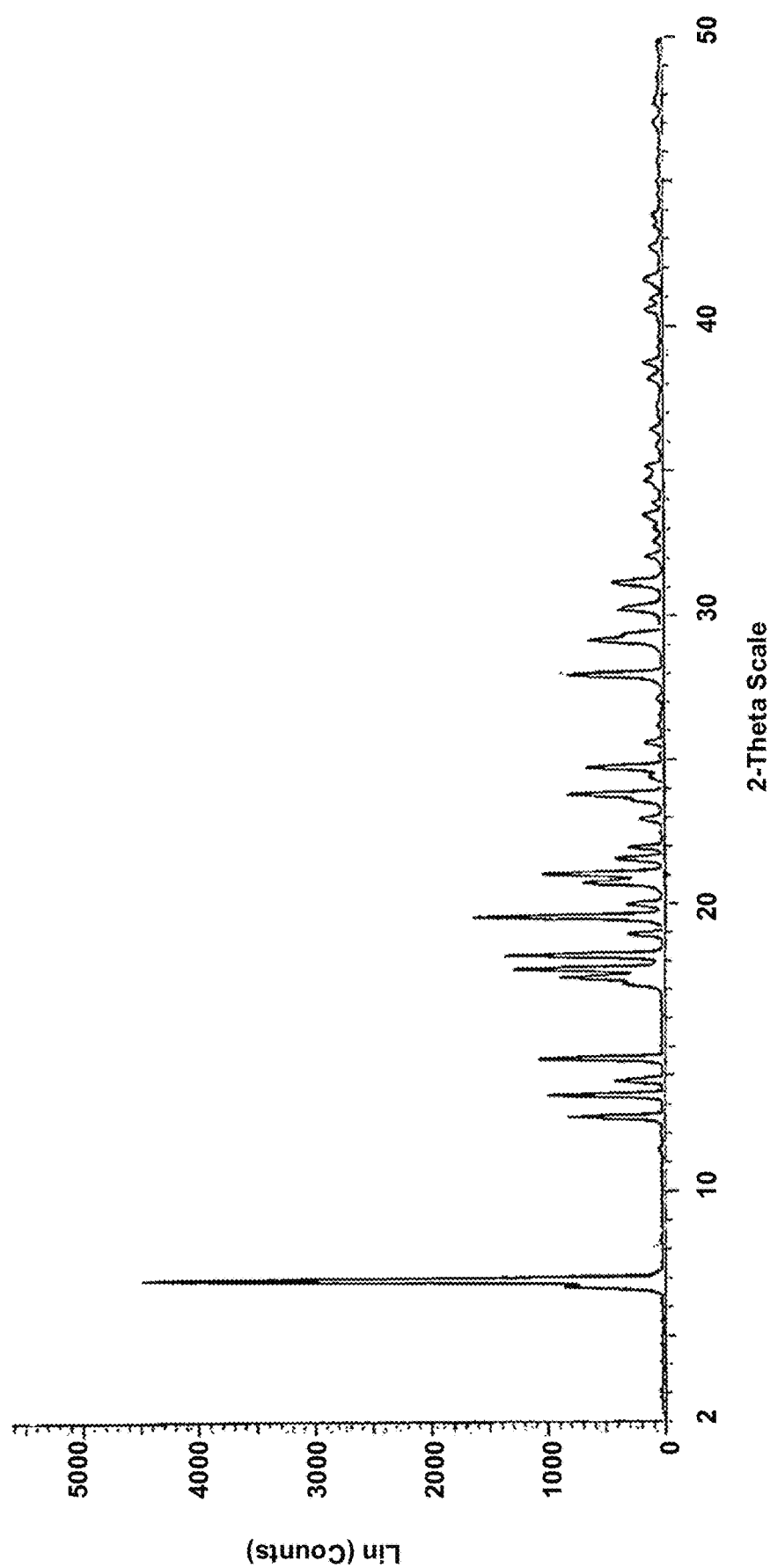
FIG. 1: X-ray powder diffraction pattern of crystalline Bictegravir Potassium Form HN1.

In another aspect of the present invention provides crystalline Bictegravir potassium Form HN1 which has a powder X-ray diffraction pattern having characteristic peaks at °2θ at about 6.8 and 18.1±0.2°; and characterized by a PXRD pattern as shown in FIG. 1.

Figure 2:
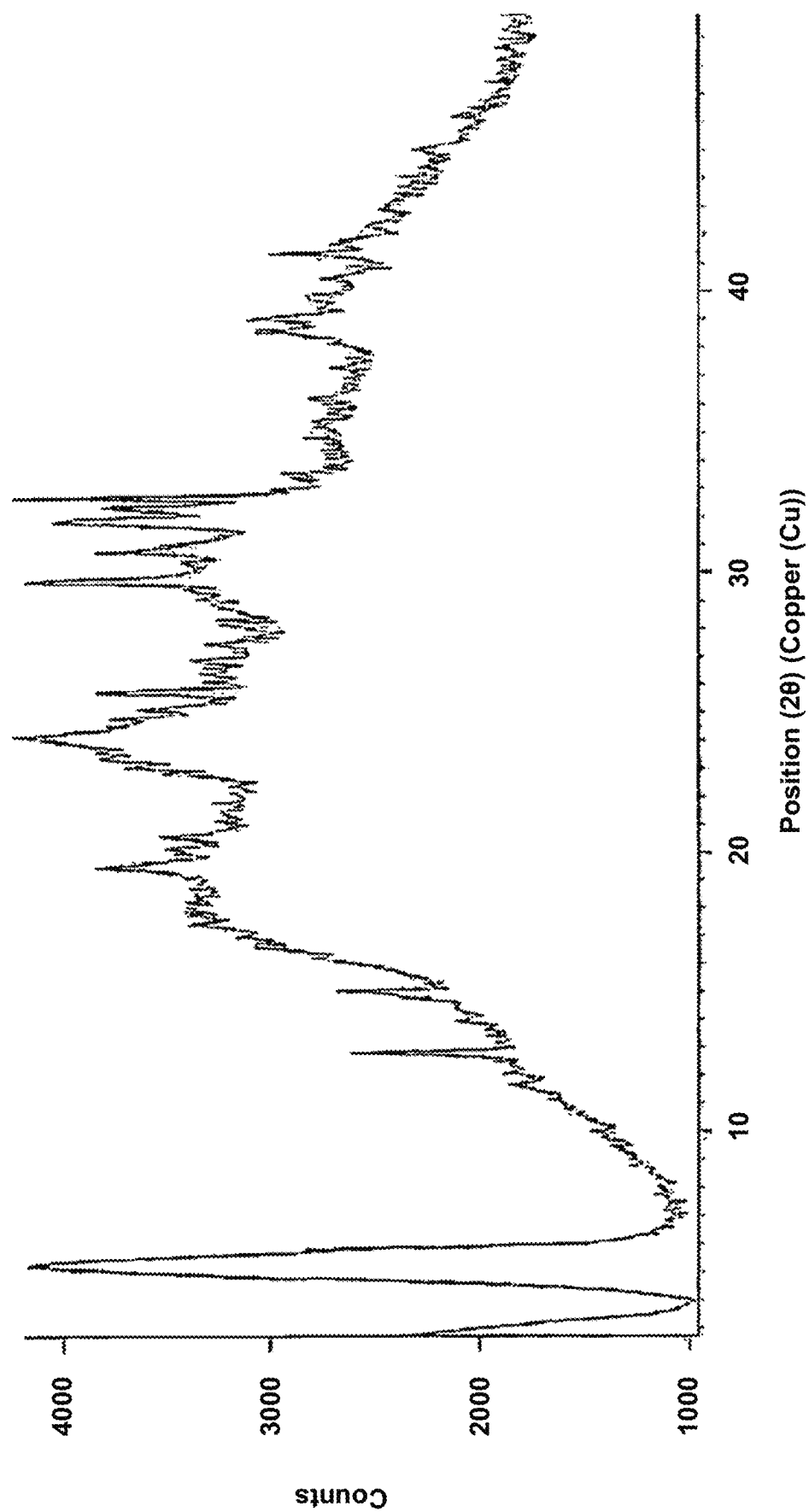
FIG. 2: X-ray powder diffraction pattern of crystalline Bictegravir Potassium Form HN2.

In another aspect of the present invention relates to crystalline Bictegravir potassium Form HN2 which has a powder X-ray diffraction pattern having characteristic peaks at °2θ at about 5.2 and 5.8±0.2°; and characterized by a PXRD pattern as shown in FIG. 2.

In another aspect of the present invention provides a process for the preparation of crystalline Bictegravir potassium Form HN1, which comprises dissolving Bictegravir in a solvent selected from group comprising of halogenated hydrocarbon, water at 25-30° C., wherein halogenated hydrocarbon solvent is selected from group comprising of methylene dichloride, ethylene dichloride, chloroform or mixtures thereof, optionally treating with carbon. Adding alcohol selected from group comprising of methanol, ethanol, n-propanol, isopropanol, n-butanol, isobutanol, 2-butanol, tertiary butanol or mixtures thereof to the filtrate and adding source of potassium selected from group comprising of potassium hydroxide, potassium t-butoxide, potassium methoxide, potassium carbonate, potassium acetate, potassium phosphate or mixtures thereof for 40-45 minutes; stirring for 2-3 hours at 25-30° C., and isolating the Bictegravir potassium crystalline Form HN1 characterized by Powder X-Ray diffraction pattern as shown in FIG. 1, having the °2θ characteristic peaks at 6.8 and 18.1±0.2°.

In another aspect of the present invention provides a process for the preparation of crystalline Bictegravir potassium Form HN2, which comprises dissolving Bictegravir in halogenated hydrocarbon solvent, water and mixtures thereof; wherein halogenated hydrocarbon solvent is selected from group comprising of methylene dichloride, ethylene dichloride, chloroform or mixtures thereof, stirring at 25-30° C. and optionally treating organic layer with carbon. Adding source of potassium selected from group comprising of potassium hydroxide, potassium t-butoxide, potassium methoxide, potassium carbonate, potassium acetate, potassium phosphate or mixtures thereof for 40-45 minutes; stirring for 2-3 hours at 25-30° C. and isolating the Bictegravir potassium crystalline Form HN2 characterized by Powder X-Ray diffraction pattern as shown in FIG. 2, having the °2θ characteristic peaks at 5.2 and 5.8±0.2°.

In another aspect of the present invention the source of potassium is added as a solid or as a solution in a suitable solvent. Source of potassium may be added lot wise or at a time to the filtrate.

In another aspect of the present invention isolation is carried out by methods including evaporation of solvent, drying and filtration techniques.

In another aspect of the present invention Bictegravir free base has been prepared by following the process known in the prior art.

In another aspect of the present invention Bictegravir potassium crystalline Form HN1 is stable at 5±3° C. and 25±2° C./60±5% RH (Relative humidity) and has the following stability data:

|  | PXRD | | Purity | | Water | |
| --- | --- | --- | --- | --- | --- | --- |
|  | 5 ± 3° C. | 25 ± 2° C./RH 60 ± 5% | 5 ± 3° C. | 25 ± 2° C./RH 60 ± 5% | 5 ± 3° C. | 25 ± 2° C./RH 60 ± 5% |
| Initial | Form HN1 | Form HN1 | 99.88 | 99.88 | 2.2 | 2.2 |
| 1st month | Form HN1 | Form HN1 | 99.87 | 99.87 | 2.8 | 2.8 |
| 3rd month | Form HN1 | Form HN1 | 99.81 | 99.80 | 2.8 | 2.9 |
| 6th month | Form HN1 | Form HN1 | 99.81 | 99.81 | 2.8 | 2.8 |

The stability of samples was tested by PXRD, HPLC and water content was measured by Karl Fischer method.

The stability test revealed no change in PXRD pattern and also in water content. There is no significant decrease in purity after storage, indicating that crystalline Form HN1 of Bictegravir potassium is physically and chemically stable at 5±3° C. and 25±2° C./60±5% RH The invention of the present application will be explained in more detail with reference to the following examples, which should not be construed as limiting the scope of the invention in any manner.

EXAMPLES

Reference Example

Preparation of (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide Step 1

1-(2,2-dimethoxyethyl)-5-methoxy-6-(methoxycarbonyl)-4-oxo-1,4-dihydropyridine-3-carboxylic acid (3.15 g, 10 mmol) in acetonitrile (36 mL) and acetic acid (4 mL) was treated with methanesulfonic acid (0.195 mL, 3 mmol) and placed in a 75 deg C. bath. The reaction mixture was stirred for 7 h, cooled and stored at −10° C. for 3 days and reheated to 75° C. for an additional 2 h. This material was cooled and carried on crude to the next step.

Step 2

Crude reaction mixture from step 1 (20 mL, 4.9 mmol) was transferred to a flask containing (1R,3S)-3-aminocyclopentanol (0.809 g, 8 mmol). The mixture was diluted with acetonitrile (16.8 mL), treated with potassium carbonate (0.553 g, 4 mmol) and heated to 85° C. After 2 h, the reaction mixture was cooled to ambient temperature and stirred overnight. 0.2M HCl (50 mL) was added, and the clear yellow solution was extracted with dichloromethane (2×150 mL). The combined organic layers were dried over sodium sulfate, filtered and concentrated to 1.49 g of a light orange solid. Recrystallization from dichloromethane:hexanes afforded the desired intermediate: LCMS-ESI+ (m/z): [M+H]+ calculated for C15H17N2O6: 321.11; found: 321.3.

Step 3

Intermediate of step 2 (0.225 g, 0.702 mmol) and (2,4,6-trifluorophenyl)methanamine (0.125 g, 0.773 mmol) were suspended in acetonitrile (4 mL) and treated with N,N-diisopropylethylamine (DIPEA) (0.183 mmol, 1.05 mmol). To this suspension was added (dimethylamino)-N,N-dimethyl(3H-[1,2,3]triazolo[4,5-b]pyridin-3-yloxy)methaniminium hexafluorophosphate (HATU, 0.294 g, 0.774 mmol). After 1.5 hours, the crude reaction mixture was taken on to the next step. LCMS-ESI+ (m/z): [M+H]+ calculated for C22H21F3N3O5: 464.14; found: 464.2.

Step 4

To the crude reaction mixture of the previous step was added MgBr2 (0.258 g, 1.40 mmol). The reaction mixture was stirred at 50° C. for 10 minutes, acidified with 10% aqueous HCl, and extract twice with dichloromethane. The combined organic phases were dried over MgSO4, filtered, concentrated, and purified by silica gel chromatography (EtOH/dichloromethane) followed by HPLC (ACN/H2a with 0.1% TFA modifier) to afford (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide: 1H-NMR (400 MHZ, DMSO-d6) δ 12.43 (s, 1H), 10.34 (t, J=5.7 Hz, 1H), 8.42 (s, 1H), 7.19 (t, J=8.7 Hz, 2H), 5.43 (dd, J=9.5, 4.1 Hz, 1H), 5.08 (s, 1H), 4.66 (dd, J=12.9, 4.0 Hz, 1H), 4.59 (s, 1H), 4.56-4.45 (m, 2H), 4.01 (dd, J=12.7, 9.7 Hz, 1H), 1.93 (s, 4H), 1.83 (d, J=12.0 Hz, 1H), 1.56 (dt, J=12.0, 3.4 Hz, 1H). LCMS-ESI+ (m/z): [M+H]+ calculated for C21H19F3N3O5: 450.13; found: 450.2.

Example 1

Preparation of Crystalline Bictegravir Potassium Form HN1

Bictegravir (50 gm) was taken in methylene dichloride (500 ml) at 25-30° C. and stirred for 15-20 minutes. Added DM water (250 ml), stirred and separated the layers. Organic layer was treated with carbon, filtered and washed with methylene dichloride. To the filtrate ethanol (90 ml) was added. Potassium hydroxide (6.85 gm) was added to the above filtrate for 45 minutes, stirred for 2 hours. The solid thus obtained was filtered, washed and dried to yield Bictegravir potassium Form HN1.

Yield: 49 gm

Example 2

Preparation of Crystalline Bictegravir Potassium Form HN2

Bictegravir (50 gm) was taken in methylene dichloride (500 ml) at 25-30° C. and stirred for 15-20 minutes. Added DM water (250 ml), stirred and separated the layers. Organic layer was treated with carbon, filtered and washed with methylene dichloride. Potassium hydroxide (6.85 gm) was added to the above filtrate for 45 minutes, stirred for 2 hours. The solid thus obtained was filtered, washed and dried to yield Bictegravir potassium Form HN2.

Yield: 49 gm

We claim:

1. Bictegravir potassium crystalline Form HN1 having an X-ray powder diffraction pattern shown in FIG. 1 and having characteristic 2θ peaks at 6.8 and 18.1±0.2°.

2. A process for preparing the Bictegravir potassium crystalline Form HN1 of claim 1, which comprises:
   a. dissolving Bictegravir in a solvent;
   b. adding a potassium source to the solvent; and
   c. isolating the Bictegravir potassium crystalline Form HN1;
   wherein the solvent is selected from the group consisting of halogenated hydrocarbon solvent, water, alcohol and mixtures thereof.

3. The process according to claim 2, wherein the potassium source is selected from the group consisting of potassium hydroxide, potassium t-butoxide, potassium methoxide, potassium carbonate, potassium acetate, potassium phosphate and mixtures thereof.

4. The process according to claim 2, wherein the solvent is a halogenated hydrocarbon solvent selected from the group consisting of methylene dichloride, ethylene dichloride, chloroform and mixtures thereof.

5. The process according to claim 2, wherein the solvent is an alcohol selected from the group consisting of methanol, ethanol, n-propanol, isopropanol, n-butanol, isobutanol, 2-butanol, tertiary butanol and mixtures thereof.

6. Bictegravir potassium crystalline Form HN2 having an X-ray powder diffraction pattern shown in FIG. 2 and having characteristic 2θ peaks at 5.2 and 5.8±0.2°.

7. A process for the preparing Bictegravir potassium crystalline Form HN2 of claim 6, which comprises:
   a. dissolving of Bictegravir in a solvent selected from a halogenated hydrocarbon solvent, water and mixtures thereof;
   b. adding a potassium source to the solvent;
   c. isolating the Bictegravir potassium crystalline Form HN2.

8. The process according to claim 7, wherein the potassium source is selected from the group consisting of potassium hydroxide, potassium t-butoxide, potassium methoxide, potassium carbonate, potassium acetate, potassium phosphate and mixtures thereof.

9. The process according to claim 7, wherein the solvent is a halogenated hydrocarbon solvent selected from the group consisting of methylene dichloride, ethylene dichloride, chloroform and mixtures thereof.

* * * * *